United States Patent [19]

Spencer

[11] Patent Number: 4,564,479
[45] Date of Patent: Jan. 14, 1986

[54] PROCESS FOR THE PD-CATALYZED ARYLATION OF OLEFINS WITH ARYL HALIDES

[75] Inventor: Alwyn Spencer, Basel, Switzerland

[73] Assignee: Ciba-Geigy Corporation, Ardsley, N.Y.

[21] Appl. No.: 437,704

[22] Filed: Oct. 29, 1982

[30] Foreign Application Priority Data

Nov. 4, 1981 [CH] Switzerland ............... 7055/81

[51] Int. Cl.$^4$ ............ C07C 121/50; C07C 69/76; C07D 407/00; C07D 319/06; C07D 317/00
[52] U.S. Cl. ............... 260/465 H; 549/370; 549/373; 549/374; 549/375; 549/448; 549/451; 549/453; 549/454; 560/104
[58] Field of Search .......... 260/465 H, 465 K; 560/104; 549/370, 373, 374, 375, 448, 451, 453, 454

[56] References Cited

U.S. PATENT DOCUMENTS 3,922,299 11/1975 Heck ............... 560/104
4,335,055 6/1982 Blaser et al. ............... 260/465 K Primary Examiner—Delbert R. Phillips Attorney, Agent, or Firm—Edward McC. Roberts; Kevin T. Mansfield; Irving M. Fishman

[57] ABSTRACT

Compounds of the formula I

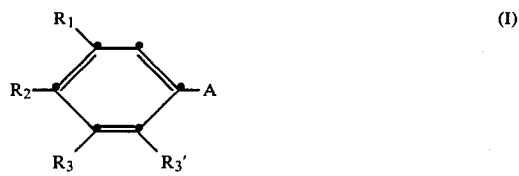

in which A is $C_{2-12}$-alkenyl, $C_{4-8}$-cycloalkenyl or a grouping—$C(R)=C(R')$—Y and Y, R, R', $R_1$, $R_2$, $R_3$ and $R_3'$ are as defined in patent claim 1, can be prepared in high yields in a simple and economical manner by reacting corresponding bromobenzenes or iodobenzenes with a compound HA in the presence of an alkali metal salt or alkaline earth metal salt of an aliphatic monocarboxylic acid having 1-12 C atoms or benzoic acid, of a cyclic or N,N-disubstituted amide as the solvent, particularly N,N-dimethylformamide, and of a palladium compound which can, if desired, contain arsenic or phosphorus, as the catalyst.

19 Claims, No Drawings

PROCESS FOR THE PD-CATALYZED ARYLATION OF OLEFINS WITH ARYL HALIDES

The invention relates to a novel process for the Pd-catalysed arylation of olefins with aryl halides.

Organic compounds having vinylic or allylic substituents, inter alia styrenes and/or stilbenes, can be prepared by a catalytic reaction of appropriate halides with olefins, for example methyl acrylate or ethylene, in the presence of tertiary amines. Catalysts used are preferably mixtures of palladium acetate and triphenylphosphine or tri-o-tolylphosphine. The reaction can be carried out with or without the addition of organic solvents, such as methanol, acetonitrile, N,N-dimethylformamide, N,N-dimethylacetamide or excess olefin. When halogenobenzenes are reacted with ethylene under pressure, styrenes and/or stilbenes are formed, depending on the reaction conditions and/or the starting halogenobenzenes [cf, for example, U.S. Pat. No. 3,922,299 and J.Org.Chem., 43, 2454 and 43, 2941 (1978)]. According to Bull.Chem.Soc. Japan, 46, 1505 (1973), various olefins, inter alia ethylene or propylene, can be arylated in the presence of palladium black or $PdCl_2$ and an excess of potassium acetate, as an acid acceptor, using methanolic solutions of halogenobenzenes, particularly iodobenzenes. In these previously known processes, the palladium compound is employed in a quantity of at least 1 mol %, based on the halogenobenzene.

The invention relates to a novel process for the Pd-catalysed arylation of olefins with aryl halides, which provides styrene and/or stilbene derivatives in good to very good yields at very low concentrations of palladium and with relatively short reaction times.

Compounds of the formula I

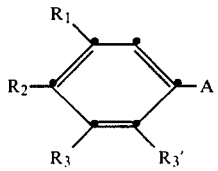

in which A is $C_{2-12}$-alkenyl, $C_{4-8}$-cycloalkenyl or a group $$-\overset{R}{\underset{|}{C}}=\overset{R'}{\underset{|}{C}}-Y,$$

Y is —CN, —COR", —COOH, —COOR", —CON(R")$_2$ or

R is hydrogen, methyl, —CN or —COOR", R' is hydrogen, methyl or —CH$_2$COOR", R" is $C_{1-12}$-alkyl or phenyl and $R_1$ and $R_3$ independently of one another are hydrogen, phenyl, $C_{1-8}$-alkyl, $C_{1-5}$-alkoxy, —CH(OCH$_3$)$_2$, —CH(OC$_2$H$_5$)$_2$,

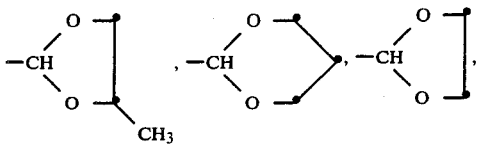

—OH, halogen, —NO$_2$, —CN, —CHO, —CO—C$_{1-4}$-alkyl, —COO—C$_{1-4}$-alkyl, —NHCO—C$_{1-4}$-alkyl, —NH$_2$, —NH—C$_{1-4}$-alkyl, —N(C$_{1-4}$-alkyl)$_2$ or —SO$_3^-$M$^+$, $R_2$ can have the same meaning as $R_1$ or $R_3$ or is a group of —CH=N-phenyl,

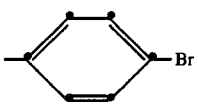

or —C(R$_4$)=C(R$_5$)(R$_6$) and $R_3'$ is hydrogen, methyl, —CN, —CHO or —SO$_3$-phenyl or $R_1$ and $R_2$ are hydrogen and $R_3$ and $R_3'$ together are —CH=CH—CH=CH—, $R_4$ is hydrogen, $C_{1-4}$-alkyl, —CN or —COO—C$_{1-4}$-alkyl, $R_5$ is hydrogen, $C_{1-4}$-alkyl, —NHCHO, —(CH$_2$)$_m$—COO—C$_{1-4}$-alkyl or —(CH$_2$)$_m$—CN in which m=1 to 4, $R_6$ is —CN or —COO—C$_{1-4}$-alkyl and M$^+$ is a metal cation, particularly an alkali metal cation, such as K$^+$ or especially Na$^+$, can be prepared by the process according to the invention by reacting a compound of the formula II

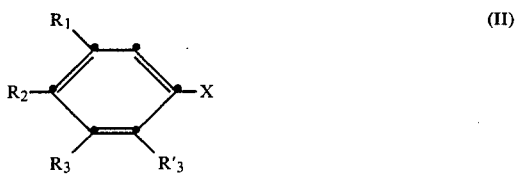

in the presence of an alkali metal salt or alkaline earth metal salt of an aliphatic monocarboxylic acid having 1-12 C atoms or benzoic acid, a cyclic or N,N-disubstituted amide, as the solvent, and of a palladium compound which can, if desired, contain arsenic or phosphorus, as the catalyst, with a compound of the formula III $$HA \qquad (III)$$

A, Y, R, R', $R_1$, $R_2$, $R_3$ and $R_3'$ being as defined under formula I, X being iodine and especially bromine and the palladium content being 0.1 to 0.0001 mol %, preferably 0.05 to 0.0001 mol %, based on the compound of the formula II. A palladium content of 0.01 to 0.001 mol % is particularly preferable, and especially 0.003 to 0.008 mol %, based on the compound of the formula II.

If A in formula I is alkenyl having 3-12 C atoms or $C_{4-8}$-cycloalkenyl, a displacement of the double bond can take place in the reaction, and mixtures of isomers are generally formed.

Preferably, at least one of R and R' is hydrogen.

Alkyl groups R" and $R_1$ to $R_5$, alkoxy groups $R_1$ to $R_3$ and alkyl groups in substituents $R_1$ to $R_6$ can be straight-chain or branched. The following may be mentioned as examples of groups R" and $R_1$ to $R_3$ according to the definition: methyl, ethyl, n-propyl, isopropyl, b-butyl, sec.-butyl, n-pentyl, 2-pentyl, n-hexyl, n-heptyl, n-octyl and n-decyl; methoxy, ethoxy, n-propoxy, isopropoxy, n-butoxy and n-pentyloxy; the carbomethoxy, carboethoxy, carbo-n-propoxy, carboisopropoxy, carbo-n-butoxy and carbo-sec.-butoxy groups; the acetamide, propionamide, butyramide and valeramide groups; the N-methylamino, N-ethylamino, N-n-propylamino and N-n-butylamino groups; the N,N-dimethylamino, N,N-diethylamino, N,N-di-n-propylamino, N,N-di-n-butylamino, N-methyl-N-ethylamino, N-methyl-N-n-propylamino and N-ethyl-N-n-butylamino groups; and —SO$_3^-$Na$^+$. Suitable groups —C(R$_4$)=C(R$_5$)(R$_6$) are preferably those in which at least one of R$_4$ and R$_5$ is hydrogen, for example —CH=C(COOCH$_3$)—CH$_2$COOCH$_3$, —CH=C(CH$_3$)COOCH$_3$, —CH=C(CH$_3$)COOC$_2$H$_5$, —C(COOCH$_3$)=CHCOOCH$_3$, —CH=C(CN)CH$_2$CH$_2$CN, —CH=CHCOOC$_2$H$_5$ and —CH=CH—CN.

If R$_1$, R$_2$ or R$_3$ are halogen, they are, for example, Cl, Br, F or I, halogen substituents R$_1$, R$_2$ or R$_3$ being preferably different from X, for example R$_1$, R$_2$ or R$_3$=Br and X=I.

If X and one of R$_1$ to R$_3$ are bromine or

both of the bromine atoms are reacted.

Alkyl groups R″ preferably have 1–8 C atoms, particularly 1–4 C atoms. Particularly preferentially, R″ is methyl, ethyl, or n-propyl.

Alkyl groups R$_1$ to R$_3$ are preferably straight-chain and have 1–4 C atoms, particularly 1 or 2 C atoms. Alkoxy groups R$_1$ to R$_3$ which are preferred are the methoxy and ethoxy groups. Methyl and ethyl are preferred as alkyl groups R$_4$ and R$_5$ and as alkyl substituents in groups R$_1$ to R$_6$.

If Y represents a group

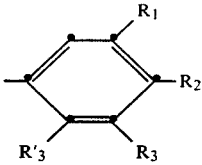

the substituents thereof R$_1$, R$_2$, R$_3$ and R$_3$′ can be the same as the corresponding substituents on the compound of the formula II or can be different therefrom, whereby symmetrical or assymetrical stilbene derivatives are formed. Stilbene derivatives can also be prepared by reacting ethylene, as the compound of the formula III, with identical or different compounds of the formula II. In general, the preparation of cinnamic acid derivatives is preferred.

It is particularly preferable to use compounds of the formula II in which X is bromine, R$_3$′ is hydrogen, R$_1$ and R$_3$ independently of one another are hydrogen, phenyl, C$_{1-3}$-alkyl, particularly methyl, methoxy, —NO$_2$, —CN, —CHO, Br, Cl, I, —NHCO—C$_{1-2}$-alkyl, —COO—C$_{1-2}$-alkyl, —CO—C$_{1-2}$-alkyl or —N(C$_{1-2}$-alkyl)$_2$ and R$_2$ can have the same meaning as R$_1$ or R$_3$ or is

or a group —C(R$_4$)=C(R$_5$)(R$_6$) in which R$_4$ is hydrogen, —COOCH$_3$ or —COOC$_2$H$_5$, R$_5$ is hydrogen, methyl, ethyl, —CH$_2$COOCH$_3$, —CH$_2$COOC$_2$H$_5$ or —CH$_2$CH$_2$CN and R$_6$ is —CN, —COOCH$_3$ or —COOC$_2$H$_5$, one of R$_4$ and R$_5$ being preferably hydrogen.

It is particularly preferable to use compounds of the formula II in which X is bromine, R$_1$, R$_3$ and R$_3$′ are hydrogen and R$_2$ is hydrogen, phenyl,

methyl, methoxy, —CN, —NO$_2$, —CHO, Br, Cl, I, —NHCOCH$_3$, —N(CH$_3$)$_2$ or a group —CH=CH—R$_6$ and R$_6$ is —CN, —COOCH$_3$ or —COOC$_2$H$_5$.

It is preferable to use, as compounds of the formula III, those in which A is alkylene having 2–8 C atoms, cyclopentylene and especially cyclohexylene or a group

one of R and R′ is hydrogen and the other is methyl or both are hydrogen, and Y is phenyl, —CN or —COOR″ in which R″ is phenyl or C$_{1-4}$-alkyl, particularly methyl or ethyl. It is particularly preferable to use, as the compound of the formula III, ethylene, acrylonitrile, methyl acrylate or ethyl acrylate.

Styrene and/or stilbene derivatives can be formed in the reaction with ethylene. The reaction can be controlled mainly by varying the pressure applied. Stilbenes are chiefly formed at a pressure between 0.1 and 1 bar (normal pressure), whereas styrene derivatives are mainly formed at higher pressures, advantageously at a pressure between 5 and 15 bar.

The preparation of stilbene derivatives of the formula

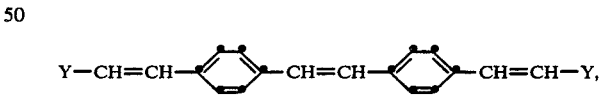

in which Y is —COOC$_2$H$_5$ and especially —CN, and, in particular, of 4-formylcinnamonitrile and of 4,4′-stilbenedialdehyde, is very particularly preferred.

Examples of alkali metal salts or alkaline earth metal salts (bases) which are suitable for use in the process according to the invention are the corresponding sodium, potassium, lithium, barium, magnesium and calcium salts, such as the acetates, propionates, butyrates, laurates and benzoates. It is preferable to use salts according to the definition which are at least partially soluble in the reaction medium. The acetates, propionates and benzoates, especially potassium acetate and very particularly sodium acetate, are particularly preferred.

Suitable cyclic or N,N-disubstituted amides are, in particular, compounds of the formula IV

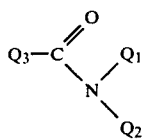

in which $Q_1$ and $Q_2$ independently of one another are straight-chain or branched $C_{1-8}$-alkyl, $C_{5-8}$-cycloalkyl or benzyl or together are —$(CH_2)_3$—, —$(CH_2)_4$— or —$(CH_2)_2$—O—$(CH_2)_2$— and $Q_3$ is hydrogen or straight-chain or branched $C_{1-8}$-alkyl or, together with $Q_1$, is —$(CH_2)_q$— in which $q=3$, 4 or 5.

Alkyl groups $Q_1$ and $Q_2$ preferably have 1–5 C atoms, in particular 1–3 C atoms. If $Q_1$ and/or $Q_2$ are cycloalkyl groups, they are, in particular, cyclopentyl or cyclohexyl. Alkyl groups $Q_3$ preferably have 1 or 2 C atoms. The following may be mentioned as examples of compounds of the formula IV: N,N-dimethylformamide, N,N-diethylformamide, N,N-di-n-butylformamide, N,N-diisopentylformamide, N,N-dimethylacetamide, N,N-dimethylpropionamide, N-methyl-N-benzylformamide, N-ethyl-N-cyclohexylformamide, N-formylpiperidine, N-formylpyrrolidone, N-acetylmorpholine, N-methylpyrrolidone, N-ethyl-pyrrolidone and N-methyl-piperidone. N,N-dimethylformamide, N,N-diethylformamide, N,N-dimethylacetamide or N-methyl-pyrrolidone are preferably used as the solvent. N,N-dimethylformamide is very particularly preferred. Furthermore, good results are also obtained in hexamethylphosphoric acid triamide as the solvent.

Examples of catalysts which can be used are palladium complexes of the type described in U.S. Pat. No. 3,922,299, in particular palladium(II) complexes, for example complexes of $PdCl_2$, $PdBr_2$, $Pd(CN)_2$, $Pd(NO_3)_2$, $Pd(CH_3COCHCOCH_3)_2$ or $Pd(OOC-C_{1-12}-alkyl)_2$, particularly palladium acetate, or palladium(O) complexes, for example complexes of bis-(dibenzylideneacetone)-palladium(O) and bis-(phenylisonitrile)-palladium(O), with trivalent phosphorus or arsenic compounds, such as trialkyl-, triaryl-, trialkoxy- and triphenoxy-phosphines or trialkyl-, triaryl-, trialkoxy- and triphenoxy-arsines or trivalent phosphorus or arsenic compounds containing mixed substituents. The following may be mentioned as examples of such phosphorus or arsenic compounds: triphenylarsine, diphenylmethylphosphine, diphenylmethoxyphosphine, trimethylphosphine, triethylphosphine, tri-n-butylphosphine, triphenylphosphine, phenyl-di-n-butoxyphosphine, tri-o-tolylphosphine and triphenyl phosphite. The said complexes can be employed as such or can be formed in situ, ie. in the reaction medium.

The phosphorus or arsenic ligand is advantageously used in a 2-fold to 10-fold molar excess, based on the palladium. In the case of compounds of the formula II which have strongly electron-attracting substituents, such as —$NO_2$, —CHO or —CN, it is also possible to carry out the reaction without a phosphorus or arsenic ligand. If X in formula II is iodine, the ligand is generally not concomitantly used. Catalysts which were used preferentially are mixtures of $PdCl_2$, palladium acetate or bis-(dibenzylideneacetone)-palladium(O) and tri-n-butylphosphine, triphenylphosphine, tri-o-tolylphosphine or triphenyl phosphite. Mixtures of palladium acetate and triphenylphosphine or tri-o-tolylphosphine are particularly preferred and diacetato-bis-(tris-o-tolylphosphine)-palladium(II) is very particularly preferred.

The reaction temperatures for the reaction according to the invention are advantageously between 50° and 200° C., preferably between 100° and 150° C.

High yields at low catalyst concentrations are achieved, in particular, if the process according to the invention is carried out in N,N-dimethylformamide as the solvent, using potassium acetate or sodium acetate as the base, and a mixture of palladium acetate and triphenylphosphine or tri-o-tolylphosphine and, especially, diacetato-bis-(tri-o-tolylphosphine)-palladium(II) as the catalyst.

The compounds which can be prepared in accordance with the invention and their uses are to a large extent known. They can, for example, be employed directly as fluorescent brighteners or as intermediates for fluorescent brighteners. Examples of fluorescent brighteners of this type are described in U.S. Pat. No. 4,108,887. The compounds which have been prepared in accordance with the invention can also be converted into dyes or fluorescent brighteners in a manner known per se, if desired by introducing suitable functional groups, such as amino groups, and/or by sulfonating the aromatic radicals [cf, for example, Encyclopedia of Chemical Technology, 2nd edition, volume 19, pages 1–16]. Stilbenes and stilbene derivatives are also used as scintillators, additives for adhesives, insecticides or light stabilisers; cf, for example, Chemical Abstracts, 78, 39,352; 84, 137,386 and 85, 22,416. Styrenes and styrene derivatives are also suitable for the preparation of homopolymers and copolymers.

In the examples which follow, the Pd content is based on the particular compound of the formula II.

$$\text{Conversion figure} = \frac{\text{mols of end product}}{\text{mols of Pd compound}}.$$

EXAMPLE 1

A stock solution of 0.0561 g ($2.5 \times 10^{-4}$ mol) of palladium acetate and 0.304 g ($10^{-3}$ mol) of tri-o-tolylphosphine in 100 ml of N,N-dimethylformamide (DMF) is prepared under argon. 1 ml of stock solution [containing 0.000561 g ($2.5 \times 10^{-6}$ mol) of palladium acetate, Pd content=0.01 mol %, and 0.00304 g ($10^{-5}$ mol) of tri-o-tolylphosphine], 4.63 g (25 mmols) of 4-bromobenzaldehyde, 2.08 ml (31.25 mmols) of acrylonitrile and 2.56 g (31.25 mmols) of anhydrous sodium acetate are then added, under argon, to 9 ml of DMF, and the mixture is stirred at 120° C. for 6 hours. The mixture is then poured into 100 ml of water, which is extracted with twice 25 ml of methylene dichloride, and the extract is dried for 15 minutes with 5 g of magnesium sulfate. After the methylene dichloride and a little DMF have been removed on a rotary evaporator, the crude product is distilled in vacuo. 3.2 g (20 mmols) of 4-formylcinnamonitrile are obtained in the form of a nearly white solid; yield 81% of theory (conversion figure 8100); melting point 92°–98° C.; boiling point 157°–163° C./133 Pa. Analysis for $C_{10}H_7NO$ (molecular weight 157.17): calculated C 76.42: H 4.49; N 8.91, found C 76.35; H 4.60; N 9.01. The product is a mixture of isomers consisting of approx. 77% of trans-isomer and 23% of cis-isomer.

EXAMPLE 2

The procedure described in Example 1 is repeated, but with a reaction time of 4 hours at 130° C. 3.22 g (20.5 mmols) of 4-formylcinnamonitrile are obtained, corresponding to a yield of 82% of theory (conversion figure 8150: Pd content 0.01 mol %).

EXAMPLE 3

The procedure described in Example 1 is repeated, but with a reaction time of 2.5 hours at reflux temperature. 3.30 g (21 mmols) of 4-formylcinnamonitrile are obtained, corresponding to a yield of 84% of theory (conversion figure 8400; Pd content 0.01 mol%).

EXAMPLE 4

The procedure described in Example 1 is repeated, but using a stock solution containing 0.262 g ($10^{-5}$ mol) of triphenylphosphine instead of tri-o-tolylphosphine. After a reaction time of 9 hours at 130° C., 3.30 g (21 mmols) of 4-formylcinnamonitrile are obtained, corresponding to a yield of 84% theory (conversion figure 8400; Pd content 0.01 mol %).

EXAMPLE 5

The procedure described in Example 1 is repeated, but using a stock solution containing 0.246 ml ($10^{-5}$ mol) of tri-n-butylphosphine instead of tri-o-tolylphosphine. After a reaction time of 4 hours at 130° C., 3.4 g (21.7 mmols) of 4-formylcinnamonitrile are obtained, corresponding to a yield of 87% of theory (conversion figure 8700; Pd content 0.01 mol %).

EXAMPLE 6

The procedure described in Example 1 is repeated, but using a stock solution containing 0.263 ml ($10^{-5}$ mol) of triphenyl phosphite. After a reduction time of 6.5 hours at 130° C., 3.35 g (21.3 mmols) of 4-formylcinnamonitrile are obtained, corresponding to a yield of 85% of theory (conversion figure 8500; Pd content 0.01 mol %).

EXAMPLE 7

The procedure described in Example 1 is repeated, but using a stock solution containing no phosphine. After a reaction time of 10 hours at 130° C., 3.06 g (19.5 mmols) of 4-formylcinnamonitrile are obtained, corresponding to a yield of 78% of theory (conversion figure 7800; Pd content 0.01 mol %).

EXAMPLE 8

The procedure described in Example 1 is repeated, but using a stock solution containing 0.152 g ($5 \times 10^{-6}$ mol) of tri-o-tolylphosphine. After a reaction time of 4 hours at 130° C., 3.51 g (22.36 mmols) of 4-formylcinnamonitrile are obtained, corresponding to a yield of 89% of theory (conversion figure 8900; Pd content 0.01 mol %).

EXAMPLE 9

A stock solution consisting of 0.0520 g ($6.25 \times 10^{-5}$ mol) of diacetato-bis-(tris-o-tolylphosphine)-palladium-(II) in 25 ml of DMF is prepared under argon. 1 ml of stock solution, 4.63 g (25 mmols) of 4-bromobenzaldehyde, 2.08 ml (31.25 mmols) of acrylonitrile and 2.26 g (27.5 mmols) of anhydrous sodium acetate are added, under argon, to 9 ml of DMF, and the reaction mixture is stirred at 130° C. for 4 hours. After working up as described in Example 1, 3.50 g (22.3 mmols) of 4-formylcinnamonitrile are obtained, corresponding to a yield of 89% of theory (conversion figure 8900; Pd content 0.01 mol %).

EXAMPLE 10

The procedure described in Example 9 is repeated, but using 1.83 ml (27.5 mmols) of acrylonitrile. 3.44 g (21.9 mmols) of 4-formylcinnamonitrile are obtained, corresponding to a yield of 88% of theory (conversion figure 8800; Pd content 0.01 mol %).

EXAMPLE 11

The procedure described in Example 1 is repeated, but using 4 ml instead of 9 ml of DMF. After a reaction time of 4 hours at reflux temperature, 3.11 g (19.8 mmols) of 4-formylcinnamonitrile are obtained, corresponding to a yield of 79% of theory (conversion figure 7900; Pd content 0.01 mol %).

EXAMPLE 12

The procedure described in Example 1 is repeated, but using N-methylpyrrolidone as the solvent for both the stock solution and the reaction mixture. After a reaction time of 6 hours at 130° C., 1.96 g (12.5 mmols) of 4-formylcinnamonitrile are obtained, corresponding to a yield of 50% of theory (conversion figure 5000; Pd content 0.01 mol %).

EXAMPLE 13

The procedure described in Example 12 is repeated, but using N,N-dimethylacetamide (DMA) as the solvent for both the stock solution and the reaction mixture. After a reaction time of 8 hours at 130° C., 2.28 g (14.5 mmols) of 4-formylcinnamonitrile are obtained, corresponding to a yield of 58% of theory (conversion figure 5800; Pd content 0.01 mol %).

EXAMPLE 14

A stock solution consisting of 0.0260 g ($3.125 \times 10^{-5}$ mol) of diacetato-bis-(tris-o-tolylphosphine)-palladium-(II) in 25 ml of DMF is prepared under argon. 1 ml of stock solution, 4.63 g (25 mmols) of 4-bromobenzaldehyde, 1.83 ml (27.5 mmols) of acrylonitrile and 2.26 g (27.5 mmols) of anhydrous sodium acetate was added to 4 ml of DMF under argon, and the mixture is stirred at 130° C. for 9 hours. After working up as described in Example 1, 3.25 g (20.7 mmols) of 4-formylcinnamonitrile are obtained, corresponding to a yield of 83% of theory (conversion figure 16600; Pd content 0.005 mol %).

EXAMPLE 15

The procedure described in Example 14 is repeated, but using 9 ml of DMF. After a reaction time of 6.5 hours, 3.37 g (21.5 mmols) of 4-formylcinnamonitrile are obtained, corresponding to a yield of 86% of theory (conversion figure 17200; Pd content 0.005 mol %).

EXAMPLE 16

The procedure described in Example 14 is repeated, but using a stock solution consisting of 0.0281 g ($1.25 \times 10^{-4}$ mol) of palladium acetate and 0.066 ml ($2.5 \times 10^{-4}$ mol) of triphenyl phosphite in 100 ml of DMF. After a reaction time of 7 hours, 2.57 g (16.4 mmols) of 4-formylcinnamonitrile are obtained, corresponding to a yield of 65% of theory (conversion figure 13000; Pd content 0.005 mol %).

EXAMPLE 17

The procedure described in Example 14 is repeated, but using a stock solution consisting of 0.0281 g ($1.25 \times 10^{-4}$ mol) of palladium acetate and 0.0615 g ($2.5 \times 10^{-4}$ mol) of tri-n-butylphosphine in 100 ml of DMF. After a reaction time of 7 hours, 2.84 g (18.1 mmols) of 4-formylcinnamonitrile are obtained, corresponding to a yield of 72% of theory (conversion figure 14400; Pd content 0.005 mol %).

EXAMPLE 18

46.25 g (250 mmols) of 4-bromobenzaldehyde, 18.31 ml (275 mmols) of acrylonitrile, 22.55 g (275 mmols) of anhydrous sodium acetate and 0.0104 g ($1.25 \times 10^{-5}$ mol) of diacetato-bis-(tris-o-tolylphosphine)-palladium-(II) are added to 100 ml of DMF under argon, and the reaction mixture is stirred at 130° C. for 8 hours. After working up as described in Example 1, 34.83 g (222 mmols) of 4-formylcinnamonitrile are obtained, corresponding to a yield of 89% of theory (conversion figure 17800; Pd content 0.005 mol %).

EXAMPLE 19

The procedure described in Example 10 is repeated, but using 1.81 g (27.5 mmols) of anhydrous lithium acetate. The reaction mixture is stirred under reflux until a temperature of 130° C. has been reached and is then kept at 130° C. After a reaction time of 8 hours, 2.91 g (18.5 mmols) of 4-formylcinnamonitrile are obtained, corresponding to a yield of 74% of theory (conversion figure 7400; Pd content 0.01 mol %).

EXAMPLE 20

A stock solution consisting of 0.0260 g ($3.125 \times 10^{-5}$ mol) of diacetato-bis-(tris-o-tolylphosphine)-palladium-(II) in 50 ml of DMF is prepared under argon. 1 ml of stock solution, 4.63 g (25 mmols) of 4-bromobenzaldehyde, 1.83 ml (27.5 mmols) of acrylonitrile and 2.26 g (27.5 mmols) of anhydrous sodium acetate are added to 9 ml of DMF under argon, and the reaction mixture is stirred at 130° C. for 10 hours. 2.86 g (18.2 mmols) of 4-formylcinnamonitrile are obtained, corresponding to a yield of 73% of theory (conversion figure 29200; Pd content 0.0025 mol %).

EXAMPLE 21

A stock solution consisting of 0.0208 g ($2.5 \times 10^{-5}$ mol) of diacetato-bis-(tris-o-tolylphosphine)-palladium-(II) in 25 ml of DMF is prepared under argon. The procedure described in Example 20 is then repeated, using 0.25 ml of stock solution. After a reaction time of 24 hours at 130° C., 3.1 g (19.7 mmols) of 4-formylcinnamonitrile are obtained, corresponding to a yield of 79% of theory (conversion figure 79000; Pd content 0.001 mol %).

EXAMPLE 22

A stock solution consisting of 0.208 g ($2.5 \times 10^{-4}$ mol) of diacetato-bis-(tris-o-tolylphosphine)-palladium-(II) in 100 ml of DMF is prepared under argon. 1 ml of stock solution, 5.05 g (25 mmols) of 4-bromonitrobenzene, 1.83 ml (27.5 mmols) of acrylonitrile and 2.2 g (27.5 mmols) of anhydrous sodium acetate are added to 9 ml of DMF under argon, and the reaction mixture is stirred at 130° C. for 4 hours. After working up as described in Example 1 and recrystallising the crude product from toluene/carbon tetrachloride, 3.8 g (21.8 mmols) of 4-nitrocinnamonitrile are obtained in the form of yellow crystals of melting point 202° C., in a yield of 87% of theory (conversion figure 8700; Pd content 0.01 mol %). Analysis for $C_9H_6N_2O_2$ (molecular weight 174.16): calculated C 62.07; H 3.47; N 16.09, found C 62.36; H 3.51; N 16.10.

EXAMPLE 23

A stock solution consisting of 0.0560 g ($2.5 \times 10^{-4}$ mol) of palladium acetate and 0.262 g ($10^{-3}$ mol) of triphenylphosphine in 100 ml of DMF is prepared under argon. 1 ml of stock solution, 2.61 ml (25 mmols) of bromobenzene, 2.99 ml (27.5 mmols) of ethyl acrylate and 2.26 g (27.5 mmols) of sodium acetate are added to 9 ml of DMF under argon, and the reaction mixture is stirred at 130° C. for 8 hours. After working up as described in Example 1, 2.86 g (16.25 mmols) of ethylcinnamate are obtained, corresponding to a yield of 65% of theory (conversion figure 6500; Pd content 0.01 mol %).

EXAMPLE 24

The procedure described in Example 23 is repeated, except that 0.310 g ($10^{-3}$ mol) of triphenyl phosphite is used instead of triphenylphosphine. After a reaction time of 8 hours at 130° C., 0.48 g (2.8 mmols) of ethyl cinnamate is obtained, corresponding to a yield of 11% of theory (conversion figure 1100; Pd content 0.01 mol %).

EXAMPLE 25

The procedure described in Example 23 is repeated, except that 0.202 g ($10^{-3}$ mol) of tri-n-butylphosphine is used instead of triphenylphosphine. After a reaction time of 8 hours at 130° C., 0.79 g (4.48 mmols) of ethyl cinnamate is obtained, corresponding to a yield of 18% of theory (conversion figure 1800; Pd content 0.01 mol %).

EXAMPLE 26

The procedure described in Example 23 is repeated, except that 0.304 g ($10^{-3}$ mol) of tri-o-tolylphosphine is used instead of triphenylphosphine. After a reaction time of 8 hours at 130° C., 2.99 g (17.0 mmols) of ethyl cinnamate are obtained, corresponding to a yield of 68% of theory (conversion figure 6800; Pd content 0.01 mol %).

EXAMPLE 27

The procedure described in Example 26 is repeated, but using 5.0 g (25 mmols) of 4-bromo-N,N-dimethylaniline and 2.99 ml (27.5 mmols) of ethyl acrylate. After a reaction time of 23 hours at 130° C. and working up as described in Example 1 and after recrystallising the crude product from n-hexane, 0.60 g (2.8 mmols) of ethyl 4-N,N-dimethylamino cinnamate is obtained in the form of pale yellow crystals of melting point 76° C., corresponding to a yield of 11% of theory (conversion figure 1100; Pd content 0.01 mol %). Analysis for $C_{13}H_{17}NO_2$ (molecular weight 219.28): calculated C 71.21; H 7.82; N 6.39, found C 71.47; H 7.85; N 6.47.

EXAMPLE 28

The procedure described in Example 26 is repeated, but using 4.28 g (25 mmols) of 4-bromotoluene and 2.99 ml (27.5 mmols) of ethyl acrylate. After a reaction time of 23 hours at 130° C., 0.67 g (3.5 mmols) of ethyl 4-methylcinnamate is obtained, corresponding to a yield of 14% of theory (conversion figure 1400; Pd content 0.01 mol %).

EXAMPLE 29

The procedure described in Example 26 is repeated, but using 4.79 g (25 mmols) of 4-bromochlorobenzene and 2.99 ml (27.5 mmols) of ethyl acrylate. After a reaction time of 8 hours at 130° C., 3.79 g (18.0 mmols) of ethyl 4-chlorocinnamate are obtained, corresponding to a yield of 72% of theory (conversion figure 7200; Pd content 0.01 mol %).

EXAMPLE 30

The procedure described in Example 26 is repeated, but using 5.05 g (25 mmols) of 4-bromonitrobenzene and 2.99 ml (27.5 mmols) of ethyl acrylate. After a reaction time of 3 hours at 130° C., 4.86 g (22.0 mmols) of ethyl 4-nitrocinnamate are obtained, corresponding to a yield of 88% of theory (conversion figure 8800; Pd content 0.01 mol %).

EXAMPLE 31

The procedure described in Example 26 is repeated, but using 3.12 ml (25 mmols) of 4-bromoanisole and 3.16 ml (27.5 mmols) of styrene. After a reaction time of 23 hours at 130° C. and working up as described in Example 1, 1.88 g (9.0 mmols) of 4-methoxystilbene are obtained, after recrystallising the crude product from n-hexane, in the form of white crystals of melting point 129° C.; yield 36% of theory (conversion figure 3600; Pd content 0.01 mol %). Analysis for $C_{15}H_{14}O$ (molecular weight 210.28): calculated C 85.68; H 6.71, found C 85.71; H 6.89.

EXAMPLE 32

The procedure described in Example 26 is repeated, but using 4.63 g (25 mmols) of 4-bromobenzaldehyde and 3.16 ml (27.5 mmols) of styrene. After a reaction time of 4 hours at 130° C., 3.74 g (18.0 mmols) of 4-formylstilbene are obtained, corresponding to a yield of 72% of theory (conversion figure 7200; Pd content 0.01 mol %).

EXAMPLE 33

The procedure described in Example 26 is repeated, but using 5.35 g (25 mmols) of 4-bromoacetanilide and 2.99 ml (27.5 mmols) of ethyl acrylate. After a reaction time of 12 hours at 130° C. and working up as described in Example 1, recrystallisation of the crude product from toluene gives 0.60 g (2.6 mmols) of ethyl 4-(N-acetylamino)-cinnamate as pale yellow crystals of melting point 133° C.; yield 10% of theory (conversion figure 1000; Pd content 0.01 mol %). Analysis for $C_{13}H_{15}NO_3$ (molecular weight 233): calculated C 66.92; H 6.48; N 6.01; O 20.59, found C 66.52; H 6.38; N 6.07; O 20.59.

EXAMPLE 34

The procedure described in Example 26 is repeated, but using 5.05 g (25 mmols) of 4-bromonitrobenzene and 3.41 ml (27.5 mmols) of ethyl crotonate. After a reaction time of 23 hours at 130° C. and after working up as described in Example 1 and recrystallising the crude product from methanol, 2.59 g (11.0 mmols) of ethyl 3-(4-nitrophenyl)-crotonate are obtained in the form of white crystals of melting point 75° C.; yield 44% of theory (conversion figure 4400; Pd content 0.01 mol %). Analysis for $C_{12}H_{13}NO_4$ (molecular weight 235.24): calculated C 61.27; H 5.57; N 5.96, found C 61.19; H 5.66; N 6.11.

EXAMPLE 35

The procedure described in Example 26 is repeated, but using 5.05 g (25 mmols) of 4-bromonitrobenzene and 3.43 ml (27.5 mmols) of ethyl methacrylate. After a reaction time of 8 hours at 130° C. and working up as described in Example 1, recrystallising the crude product from methanol gives 2.70 g (11.5 mmols) of ethyl α-methyl-4-nitrocinnamate in the form of yellow crystals of melting point 75° C.; yield 46% of theory (conversion figure 4600; Pd content 0.01 mol %). Analysis for $C_{12}H_{13}NO_4$ (molecular weight 235.24): calculated C 61.27; H 5.57; N 5.96, found C 61.18; H 5.57; N 6.24.

EXAMPLE 36

0.0067 g ($8.0 \times 10^{-6}$ mol) of diacetato-bis-(tris-o-tolylphosphine)-palladium(II), 0.0087 g ($3.2 \times 10^{-5}$ mol) of tri-o-tolylphosphine, 14.58 g (80 mmols) of 3-bromobenzonitrile, 5.86 ml (88 mmols) of acrylonitrile and 7.22 g (88 mmols) of anhydrous sodium acetate are added, under argon, to 32 ml of DMF, and the reaction mixture is stirred at 130° C. for 8 hours. After working up as described in Example 1 and recrystallising the crude product from isopropanol, 10.72 g (69.6 mmols) of 3-cyanocinnamonitrile are obtained in the form of white crystals of melting point 139° C.; yield 87% of theory (conversion figure 8700; Pd content 0.01 mol %). Analysis for $C_{10}H_6N_2$ (molecular weight 154.17): calculated C 77.91; H 3.92; N 18.17, found C 77.86; H 4.21; N 18.41.

EXAMPLE 37

The procedure described in Example 26 is repeated, but using 5.4 g (25 mmols) of 2-bromo-4-nitrotoluene and 1.83 ml (27.5 mmols) of acrylonitrile. After a reaction time of 8 hours at 130° C. and working up as described in Example 1, 2.53 g (13.45 mmols) of 2-methyl-4-nitrocinnamonitrile are obtained, after recrystallising the crude product from toluene/isopropanol, in the form of white needle-shaped crystals of melting point 166° C.; yield 54% of theory (conversion figure 5400; Pd content 0.01 mol %). Analysis for $C_{10}H_8N_2O_2$ (molecular weight 188.19): calculated C 63.83; H 4.29; N 14.89; O 17.00, found C 64.17; H 4.48; N 15.00; O 17.11.

EXAMPLE 38

2 ml of the stock solution described in Example 23 are added to 18 ml of DMF. 9.26 g (50 mmols) of 4-bromobenzaldehyde, 5.58 ml (55 mmols) of cyclohexene and 4.52 g (55 mmols) of anhydrous sodium acetate are then added and the reaction mixture is stirred for 8 hours at 140° C. in a pressure tube. After working up as described in Example 1, the crude product is distilled in vacuo. 2.05 g (11.0 mmols) of 4-formylphenylcyclohexene are obtained in the form of a yellow liquid of boiling point 140°–150° C./2400 Pa; yield 22% of theory (conversion figure 2200; Pd content 0.01 mol %). The product is a mixture of isomers.

EXAMPLE 39

The procedure described in Example 26 is repeated, but using 5.05 g (25 mmols) of 4-bromonitrobenzene and 4.33 ml (27.5 mmols) of 1-octene. After a reaction time of 10 hours at 130° C. and working up as described in Example 1, distillation of the crude product gives 3.90 g (16.7 mmols) of 4-nitrophenyloctene of boiling point 140°–150° C./27 Pa in the form of a yellow liquid; yield 67% of theory (conversion figure 6700; Pd content 0.01 mol %). The product is a mixture of isomers. Analysis for $C_{14}H_{19}NO_2$ (molecular weight 233.21): calculated C 70.08; H 8.21; N 6.01, found C 71.75; H 8.10; N 6.16.

EXAMPLE 40

2 ml of the stock solution described in Example 23 are added to 18 ml of DMF. 9.77 g (50 mmols) of 4-chlorobromobenzene and 4.52 g (55 mmols) of anhydrous sodium acetate are then added. The reaction mixture is then placed under ethylene in a pressure apparatus and is stirred for 6 hours at 10 bar and 130° C. 3.62 g (26.1 mmols) of 4-chlorostyrene are obtained, corresponding to a yield of 52% of theory (conversion figure 5200; Pd content 0.01 mol %).

EXAMPLE 41

The procedure described in Example 9 is repeated, but using 4.63 g (25 mmols) of 4-bromobenzaldehyde, 2.26 g (27.5 mmols) of anhydrous sodium acetate and ethylene. The reaction mixture is stirred at 130° C. for 4 hours, while passing ethylene through it under normal pressure. After working up as described in Example 1 and recrystallising the crude product from isopropanol, 1.73 g (7.33 mmols) of 4,4'-diformylstilbene are obtained in the form of yellow crystals of melting point 172° C.; yield 59% of theory (conversion figure 5900, based on the 4-bromobenzaldehyde; Pd content 0.01 mol %). Analysis for $C_{16}H_{12}O_2$ (molecular weight 236.27: calculated C 81.34; H 5.12; O 13.54, found C 81.20; H 5.36; O 13.46.

EXAMPLE 42

0.00505 g ($2.25 \times 10^{-5}$ mol) of 0.01 palladium acetate, 0.0274 g ($9 \times 10^{-5}$ mol) of tri-o-tolylphosphine, 46.8 (0.225 mol) of 4-bromocinnamonitrile and 20.3 g (0.2475 mol) of anhydrous sodium acetate are added, under argon, to 90 ml of DMF. Ethylene is then passed in under normal pressure and the reaction mixture is stirred at 130° C. for 10 hours. The crude product is extracted in a Soxhlet with toluene and is then recrystallised from DMF/water. 21.3 g (0.0755 mol) of the fluorescent brightener 4,4'-bis-(trans-2-cyanovinyl)-trans-stilbene are obtained in the form of yellow crystals of melting point 219°–221° C.; yield 67% of theory (conversion figure 6700, based on the bromoaromatic compound; Pd content 0.01 mol %). Analysis for $C_{20}H_{14}N_2$ (molecular weight 282): calculated C 85.08; H 5.00 N 9.92, found C 84.75; H 5.07; N 9.67.

EXAMPLE 43

0.0832 g ($10^{-4}$ mol) of diacetato-bis-(tris-o-tolylphosphine)-palladium(II), 118 g (0.5 mol) of 1,4-dibromobenzene, 119.2 ml (1.1 mols) of ethyl acrylate and 90.2 g (1.1 mols) of anhydrous sodium acetate are added, under argon, to 400 ml of DMF, and the reaction mixture is stirred at 130° C. for 4 hours. After working up as described in Example 1, the crude product is recrystallised from cyclohexane. 92.8 g (0.34 mol) of diethyl phenylene-1,4-bis-acrylate are obtained in the form of white crystals of melting point 95°- C.; yield 68% of theory (conversion figure 6800, based on the bromine content; Pd content 0.01 mol %). Analysis for $C_{16}H_{18}O_4$ (molecular weight 274.32): calculated C 70.06; H 6.62; O 23.33, found C 69.74; H 6.60; O 23.95.

EXAMPLE 44

The procedure described in Example 9 is repeated, but using 3.90 g (12.5 mmols) of 4,4'-dibromobiphenyl, 2.87 ml (27.5 mmols) of styrene and 2.26 g 27.5 mmols) of anhydrous sodium acetate. After a reaction time of 4 hours at 130° C., the reaction mixture is poured into 100 ml of water. The product is filtered off, washed with water and methanol and recrystallised from DMF. 3.83 g (10.7 mmols) of 4,4'-bis-(2-phenylvinyl)-biphenyl are obtained in the form of pale yellow crystals of melting point 323°–326° C.: yield 86% of theory (conversion figure 8600, based on the bromine content; Pd content 0.01 mol %). Analysis for $C_{28}H_{22}$ (molecular weight 358.48): calculated C 93.81; H 6.19, found C 93.39; H 6.08.

EXAMPLE 45

The procedure described in Example 26 is repeated, but using 3.49 ml (25 mmols) of 1-bromonaphthalene, 3.16 g (27.5 mmols) of styrene and 2.70 g (27.5 mmols) of potassium acetate. After a reaction time of 17 hours at 130° C. and working up as described in Example 1, 2.3 g (10.0 mmols) of 1-(2-phenylvinyl)-naphthalene are obtained, after recrystallising the crude product from ethanol, in the form of greenish-yellow crystals of melting point 71° C.; yield 40% (conversion figure 4000; Pd content 0.01 mol). Analysis for $C_{18}H_{14}$ (molecular weight 230.31): calculated C 93.88; H 6.13, found C 93.65; H 6.11.

EXAMPLE 46

The procedure described in Example 9 is repeated, but using 2.79 ml (25 mmols) of iodobenzene and 2.98 ml (27.5 mmols) of ethyl acrylate. After a reaction time of 4.5 hours at 130° C., 2.92 g (16.6 mmols) of ethyl cinnamate are obtained, corresponding to a yield of 66% of theory (conversion figure 6600; Pd content 0.01 mol %).

EXAMPLE 47

The procedure described in Example 46 is repeated, but without using phosphine. After a reaction time of 4.5 hours at 130° C., 2.71 g (15.4 mmols) of ethyl cinnamate are obtained, corresponding to a yield of 62% of theory (conversion figure 6200; Pd content 0.01 mol %).

EXAMPLE 48

The procedure described in Example 47 is repeated, but using 7.07 g (25 mmols) of 4-bromoiodobenzene and 1.83 g (27.5 mmols) of acrylonitrile. After a reaction time of 8 hours at 130° C., 3.95 g (19.0 mmols) of 4-bromocinnamonitrile are obtained, corresponding to a yield of 76% of theory (conversion figure 7600; Pd content 0.01 mol %).

EXAMPLE 49

11 g of a 30% sodium methylate solution are added dropwise, at room temperature and in the course of 16 minutes, to a solution of 17.5 g of 2-(4-diethoxyphosphorylmethylphenyl)-4-methoxy-6-methylpyrimidine and 7.8 g of 4-formylcinnamonitrile in 100 ml of DMF. The temperature rises to 40° C. The reaction mixture is then stirred at 45° C. for 2 hours and poured into a mixture consisting of 160 ml of methanol and 250 ml of water, and the pH of the aqueous suspension is adjusted to 7 with acetic acid. The precipitate is filtered off with suction, washed wth water and dried. 12.1 g, corresponding to 62% of theory, of the fluorescent brightener of the formula

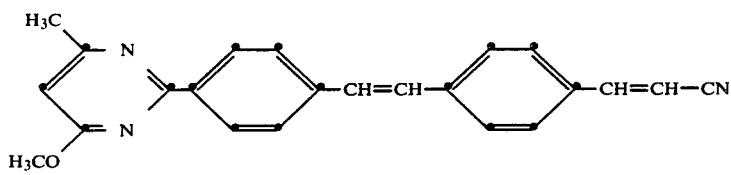

are obtained in the form of a yellowish powder of melting point 196°–197° C. after recrystallising several times from 1:1 toluene/ligroin, with the aid of bleaching earth.

EXAMPLE 50

A stock solution consisting of 0.1041 g ($1.25 \times 10^{-4}$ mol) of diacetato-bis-(tris-o-tolylphosphine)-palladium-(II) in 50 ml of hexamethylphosphoric acid triamide is prepared under argon. 1 ml of stock solution, 9.25 g (50 mmols) of 4-bromobenzaldehyde, 3.66 ml (55 mmols) of acrylonitrile and 4.51 g (55 mmols) of anhydrous sodium acetate are added, under argon, to 19 ml of hexamethylphosphoric acid triamide, and the mixture is stirred at 130° C. for 8 hours. The hexamethylphosphoric acid triamide is removed under a high vacuum and the product is distilled. 6.58 g (41.9 mmols) of 4-formylcinnamonitrile are obtained, corresponding to a yield of 84% of theory (conversion figure 16800; Pd content 0.005 mol %).

EXAMPLE 51

A stock solution consisting of 0.02244 g ($10^{-4}$ mol) of palladium acetate and 0.1216 g ($4 \times 10^{-4}$ mol) of tri-o-tolylphosphine in 20 ml of hexamethylphosphoric acid triamide is prepared under argon. 0.5 ml of stock solution, 5.2 g (25 mmols) of 4-bromocinnamonitrile and 2.26 g (27.5 mmols) of anhydrous sodium acetate are added, under ethylene, to 9.5 ml of hexamethylphosphoric acid triamide, and the mixture is stirred at 130° C. for 8 hours, while passing ethylene continuously over its surface. 50 ml of water are then added to the mixture, and the product is filtered off and washed with 50 ml of methanol. After recrystallisation from 120 ml of propionitrile, 2.02 g (7.2 mmols) of 4,4'-bis-(2-cyanovinyl)-stilbene are obtained, corresponding to a yield of 57% of theory (conversion figure 5700; Pd content 0.01 mol %) based on the bromoaromatic compound.

EXAMPLE 52

A stock solution of 0.01122 g ($5 \times 10^{-5}$ mol) of palladium acetate and 0.0608 g ($2 \times 10^{-4}$ mol) of tri-o-tolylphosphine in 20 ml of N,N-dimethylformamide (DMF) is prepared under argon. 1 ml of stock solution, 2.90 ml (25 mmols) of 2-bromobenzaldehyde, 2.98 ml (27.5 mmols) of ethyl acrylate and 2.26 g (27.5 mmols) of anhydrous sodium acetate are added, under argon, to 9 ml of DMF, and the reaction mixture is stirred at 130° C. for 6 hours. After working up as described in Example 1, the crude product is distilled in a high vacuum. 2.1 g (10.3 mmols) of ethyl o-formylcinnamate are obtained in the form of a pale brown liquid of boiling point 126°–128° C./0.4 mm, corresponding to a yield of 41% of theory (conversion figure 4100; Pd content 0.01 mol %).

EXAMPLE 53

0.67 ml of the stock solution from Example 52, 3.05 g (16.8 mmols) of 2-bromobenzonitrile, 1.99 ml (18.4 mmols) of ethyl acrylate and 1.50 g (18.4 mmols) of anhydrous sodium acetate are added, under argon, to 16.3 ml of DMF, and the reaction mixture is stirred at 130° C. for 3 hours. After working up as described in Example 1, the crude product is recrystallised from a mixture of pentane and carbon tetrachloride. 1.5 g (7.5 mmols) of ethyl o-cyanocinnamate are obtained in the form of white crystals of melting point 56° C., corresponding to a yield of 44% of theory (conversion figure 4400; Pd content 0.01 mol %). Analysis for $C_{12}H_{11}NO_2$ (molecular weight 201.23): calculated C 71.63; H 5.51; N 6.96; O 15.90, found C 71.17; H 5.64; N 6.88; O 16.56.

EXAMPLE 54

A stock solution of 0.0168 g ($7.5 \times 10^{-5}$ mol) of palladium acetate and 0.0912 g ($3 \times 10^{-4}$ mol) of tri-o-tolylphosphine in 50 ml of DMF is prepared under argon. 1 ml of stock solution, 4.71 g (15 mmols) of phenyl o-bromobenzene sulfonate, 1.79 ml (16.5 mmols) of ethyl acrylate and 1.35 g (16.5 mmols) of anhydrous sodium acetate are added, under argon, to 14 ml of DMF, and the reaction mixture is stirred at 130° C. for 5 hours. After working up as described in Example 1, the crude product is distilled in a high vacuum. 2.54 g (7.65 mmols) of ethyl o-phenoxysulfonylcinnamate are obtained in the form of a colourless liquid of boiling point 186°–190° C./0.35 mm Hg, corresponding to a yield of 51% of theory (conversion figure 5100; Pd content 0.01 mol %). Analysis for $C_{17}H_{16}SO_5$ (molecular weight 332.37): calculated C 61.44; H 4.85; O 24.07; S 9.65—found C 61.37; H 4.84; O 24.22; S 9.65.

COMPARISON EXAMPLES 4.63 g (25 mmols) of 4-bromobenzaldehyde, 2.08 ml (31.25 mmols) of acrylonitrile, 4.36 ml (31.25 mmols) of triethylamine and the quantities of palladium(II) acetate and tri-o-tolylphosphine indicated below are added, under argon, to 10 ml of propionitrile in a pressure tube. The tube is closed and the contents are shaken at 140° C. The product obtained is 4-formylcinnamonitrile. The reaction times and yields are shown in the Table below.

|   | $Pd(OAc)_2$ (mmol) | $P(o-Tolyl)_3$ (mmol) | Time (hrs) | Yield (%) | Conversion Figure |
|---|---|---|---|---|---|
| (a) | 0.25 | 1.00 | 6 | 92 | 92 |
| (b) | $2.5 \times 10^{-2}$ | $10^{-1}$ | 23 | 47 | 470 |
| (c) | $2.5 \times 10^{-3}$ | $10^{-2}$ | 23 | <2 | <200 |
| The data from Example 21 are shown for comparison |
| (d) | $2.5 \times 10^{-4}$ | $5 \times 10^{-4}$ | 24 | 79 | 79,000 |

What is claimed is:
1. A process for the preparation of a compound of formula I

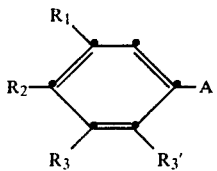 (I)

in which A is

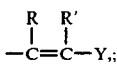

wherein Y is cyano;
R is selected from the group consisting of hydrogen, methyl, cyano, and —COOR'';
R' is selected from the group consisting of hydrogen, methyl, and —CH$_2$COOR'';
R'' is selected from the group consisting of C$_1$-C$_{12}$-alkyl and phenyl;
R$_1$, R$_2$, and R$_3$, independently of one another, are selected from the group consisting of hydrogen, phenyl, C$_1$-C$_8$-alkyl, C$_1$-C$_5$-alkoxy, —CH(OCH$_3$)$_2$, —CH(OC$_2$H$_5$)$_2$,

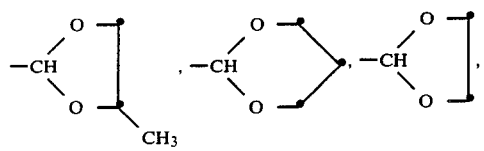

OH, halogen, nitro, cyano, —CHO, —CO, —(C$_1$-C$_4$)-alkyl, —COO—(C$_1$-C$_4$)-alkyl, —NHCO—(C$_1$-C$_4$)-alkyl, amino, —NH—(C$_1$-C$_4$)-alkyl, —N((C$_1$-C$_4$)-alkyl)$_2$ and SO$_3$M;
R$_2$ being further selected from the group consisting of —CH=N-phenyl, p-bromophenyl, and —C(R$_4$)=C(R$_5$)(R$_6$);
R$_3$' is selected from the group consisting of hydrogen, methyl, cyano, —CHO, and SO$_3$-phenyl;
R$_4$ is selected from the group consisting of hydrogen, C$_1$-C$_4$-alkyl, cyano, —COO—(C$_1$-C$_4$)-alkyl;
R$_5$ is selected from the group consisting of hydrogen, C$_1$-C$_4$-alkyl, —NHCHO, —(CH$_2$)$_m$—COO—(C$_1$-C$_4$)alkyl and —(CH$_2$)$_m$—CN, is which m is 1-4;
R$_6$ is selected from the group consisting of cyano and —COO—(C$_1$-C$_4$)-alkyl; or
R$_1$ and R$_2$ are both hydrogen and R$_3$ and R$_3$' together are —CH=CH—CH=CH—; and
M is a monovalent metal cation;
which process comprises reacting a compound of formula II

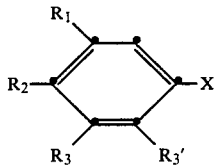 II with a compound HA in the presence of
(i) an alkali salt or alkaline earth metal salt of
(a) an aliphatic monocarboxylic acid having 1 to 12 carbon atoms or (b) benzoic acid;
(ii) a cyclic or N,N-di-substituted amine as a solvent; and
(iii) a palladium catalyst containing arsenic or phosphorous, X being selected from the group consisting of iodine and bromine; A, Y, R, R', R$_1$, R$_2$, R$_3$, and R$_3$' being as defined above, said palladium catalyst being present in an amount of 0.1 to 0.0001 mole percent based on the compound of formula II, said reaction taking place at a temperature between 50° and 200° C.

2. A process of claim 1, wherein the palladium content is 0.05 to 0.0001 mol %, in particular 0.01 to 0.001 mol %, based on the compound of the formula II.

3. A process of claim 1, wherein a compound of the formula III in which A is —C(R)=C(R')—Y and at least one of R and R' is hydrogen, is used.

4. A process of claim 1, wherein a compound of the formula II in which X is bromine, R$_3$' is hydrogen, R$_1$ and R$_3$ independently of one another are hydrogen, phenyl, C$_{1-3}$-alkyl, particularly methyl, methoxy, —NO$_2$, —CN, —CHO, Br, Cl, I, —NHCO—C$_{1-2}$-alkyl, —COO—C$_{1-2}$-alkyl, —CO—C$_{1-2}$-alkyl or —N(C$_{1-2}$-alkyl)$_2$, and R$_2$ can have the same meaning as R$_1$ or R$_3$ or is

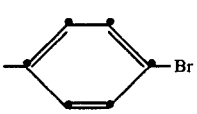

or a group —C(R$_4$)=C(R$_5$)(R$_6$) in which R$_4$ is hydrogen, —COOCH$_3$ or —COOC$_2$H$_5$, R$_5$ is hydrogen, methyl, ethyl, —CH$_2$COOCH$_3$, —CH$_2$COOC$_2$H$_5$ or —CH$_2$CH$_2$CN and R$_6$ is —CN, —COOCH$_3$ or —COOC$_2$H$_5$, one of R$_4$ and R$_5$ being hydrogen, is used.

5. A process of claim 1, wherein a compound of the formula II in which X is bromine, R$_1$, R$_3$ and R$_3$' are hydrogen and R$_2$ is hydrogen, phenyl,

methyl, methoxy, —CN, —NO$_2$, —CHO, Br, Cl, I, —NHCOCH$_3$, —N(CH$_3$)$_2$ or a group —CH=CH—R$_6$ and R$_6$ is —CN, —COOCH$_3$ or —COOC$_2$H$_5$, is used.

6. A process of claim 1, wherein a compound of the formula III in which A is alkylene having 2-8 C atoms, cyclopentylene, cyclohexylene or a group —C(R)=C(R')—Y, one of R and R' is hydrogen and the other is methyl or both are hydrogen is used.

7. A process of claim 1, wherein acrylonitrile is used as the compound of the formula III.

8. A process of claim 1, wherein a compound of the formula

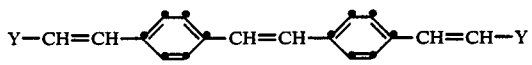

wherein Y is —CN is prepared.

9. A process of claim 1, wherein 4-formylcinnamonitrile is prepared.

10. A process of claim 1, wherein the base used is an alkali metal acetate, propionate or benzoate or an alkaline earth metal acetate, propionate or benzoate.

11. A process of claim 1, wherein the base used is potassium acetate and, in particular, sodium acetate.

12. A process of claim 1, wherein the amide used is a compound of the formula IV

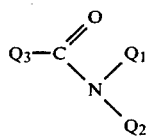

in which $Q_1$ and $Q_2$ independently of one another are straight-chain or branched $C_{1-8}$-alkyl, $C_{5-8}$-cycloalkyl or benzyl or together are —$(CH_2)_3$—, —$(CH_2)_4$— or —$(CH_2)_2$—O—$(CH_2)_2$— and $Q_3$ is hydrogen or straight-chain or branched $C_{1-8}$-alkyl or, together with $Q_1$, is —$(CH_2)_q$— in which q=3, 4 or 5.

13. A process of claim 1, wherein the solvent used is N,N-dimethylformamide, N,N-diethylformamide, N,N-dimethylacetamide, N-methylpyrrolidone or hexamethylphosphoric acid triamide.

14. A process of claim 1, wherein the catalyst used is a mixture consisting of $PdCl_2$, palladium acetate or bis-(dibenzylideneacetone)-palladium(O) and tri-n-butylphosphine, triphenylphosphine, tri-o-tolylphosphine or triphenyl phosphite.

15. A process of claim 1, wherein the catalyst used is a mixture consisting of palladium acetate and triphenylphosphine or tri-o-tolylphosphine.

16. A process of claim 1, wherein the reaction is carried out in N,N-dimethylformamide as the solvent, potassium acetate or sodium acetate is used as the base, and the catalyst used is a mixture consisting of palladium acetate and triphenylphosphine or tri-o-tolylphosphine.

17. A process of claim 1, wherein the reaction is carried out between 100° and 150° C.

18. The process according to claim 15 wherein said catalyst is diacetato-bis-(tris-o-tolylphosphine)-palladium(II).

19. The process according to claim 16 wherein said catalyst is diacetato-bis-(tris-o-tolylphosphine)-palladium(II).

* * * * *